(12) United States Patent
Kina

(10) Patent No.: US 11,612,550 B2
(45) Date of Patent: Mar. 28, 2023

(54) DECORATING POWDER COMPOSITION

(71) Applicant: SHISEIDO COMPANY, LTD., Tokyo (JP)

(72) Inventor: Toru Kina, Shizuoka (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 54 days.

(21) Appl. No.: 17/024,761

(22) Filed: Sep. 18, 2020

(65) Prior Publication Data
US 2021/0000701 A1 Jan. 7, 2021

Related U.S. Application Data

(62) Division of application No. 15/755,849, filed as application No. PCT/JP2016/079469 on Oct. 4, 2016, now abandoned.

(30) Foreign Application Priority Data

Oct. 30, 2015 (JP) .................. 2015-214128

(51) Int. Cl.
A61K 8/02 (2006.01)
A61Q 1/10 (2006.01)
A61Q 1/06 (2006.01)
A61K 8/25 (2006.01)
A61K 8/26 (2006.01)
A61K 8/27 (2006.01)
A61K 8/29 (2006.01)
A61K 8/58 (2006.01)
A61Q 1/12 (2006.01)

(52) U.S. Cl.
CPC .............. *A61K 8/022* (2013.01); *A61K 8/25* (2013.01); *A61K 8/26* (2013.01); *A61K 8/27* (2013.01); *A61K 8/29* (2013.01); *A61K 8/585* (2013.01); *A61Q 1/06* (2013.01); *A61Q 1/10* (2013.01); *A61Q 1/12* (2013.01); *A61K 2800/436* (2013.01); *A61K 2800/612* (2013.01); *A61K 2800/805* (2013.01)

(58) Field of Classification Search
None
See application file for complete search history.

(56) References Cited

U.S. PATENT DOCUMENTS

| 3,830,738 A | 8/1974 | Cottrell |
| 6,922,975 B1 * | 8/2005 | Shiraishi ................. B65B 9/042 |
| | | 53/436 |
| 2009/0035333 A1 * | 2/2009 | Sasaki ................... A61Q 19/00 |
| | | 514/772.3 |
| 2012/0082708 A1 | 4/2012 | Lee et al. |
| 2012/0156268 A1 | 6/2012 | Kawasaki |
| 2012/0251605 A1 | 10/2012 | Iimura |
| 2013/0296578 A1 | 11/2013 | Amano et al. |
| 2014/0010775 A1 | 1/2014 | Sonoyama |

FOREIGN PATENT DOCUMENTS

| CN | 103221341 A | 7/2013 |
| DE | 12746784 T1 | 5/2014 |
| EP | 2417960 A1 | 2/2012 |
| EP | 2497457 A1 | 9/2012 |
| EP | 2676930 | 12/2013 |
| JP | 2000317383 A2 | 11/2000 |
| JP | 200111301 | 1/2001 |
| JP | 2003-277231 A | 10/2003 |
| JP | 2004-292342 A | 10/2004 |
| JP | 2009155275 A2 | 7/2009 |
| JP | 201037303 | 2/2010 |
| JP | 2013189428 A2 | 9/2013 |
| KR | 20130057484 | 5/2013 |
| WO | 2012111452 A1 | 8/2012 |

OTHER PUBLICATIONS

International Search Report (ISR) dated Nov. 8, 2016 filed in PCT/JP2016/079469.
Valet et al., "Colouring Agents in Decorative and other Cosmetics. Analytical Methods", Analysis of Cosmetic Products, 2007, pp. 141-152; Cited in EPOA.
Anonymous, "Functional Materials of Titanium Dioxide", Ishihara Sangyo Kaisha, Ltd., Ishihara Techno Corp., 2018, pp. 1-6, total 8 pages; Cited in EPOA.

* cited by examiner

*Primary Examiner* — David J Blanchard
*Assistant Examiner* — Sarah J Chickos
(74) *Attorney, Agent, or Firm* — Rankin, Hill & Clark LLP

(57) ABSTRACT

[Problem] To provide a decorating powder composition for decorating the surface of a solid cosmetic material, in particular, for obtaining a solid cosmetic material having a beautiful appearance which is decorated with a glossy powder, and a decorating method using the decorating powder composition.
[Solution] Provided are a decorating powder composition including a glossy powder which has been surface-treated with a silane compound or a silazane compound, and a method for decorating a solid cosmetic material, the method including causing the decorating powder composition to adhere to a printing plate and then bringing the printing plate into contact with a surface of the solid cosmetic material to transfer the decorating powder composition to the surface of the solid cosmetic material and decorate the solid cosmetic material.

4 Claims, 4 Drawing Sheets

Fig. 4

| | STATE OF ADHESION TO PRINTING PLATE | NOTE |
|---|---|---|
| COMPARATIVE EXAMPLE 3 | | UNEVEN ADHESION, TREND TO AGGLOMERATION |
| COMPARATIVE EXAMPLE 4 | | TREND TO AGGLOMERATION |
| COMPARATIVE EXAMPLE 5 | | UNEVEN ADHESION, TREND TO AGGLOMERATION |
| COMPARATIVE EXAMPLE 6 | | UNEVEN ADHESION, TREND TO AGGLOMERATION |
| COMPARATIVE EXAMPLE 7 | | UNEVEN ADHESION, TREND TO AGGLOMERATION |
| COMPARATIVE EXAMPLE 8 | | TREND TO AGGLOMERATION |
| COMPARATIVE EXAMPLE 9 | | UNEVEN ADHESION, TREND TO AGGLOMERATION |
| COMPARATIVE EXAMPLE 10 | | UNEVEN ADHESION, TREND TO AGGLOMERATION |
| COMPARATIVE EXAMPLE 11 | | UNEVEN ADHESION, TREND TO AGGLOMERATION |
| COMPARATIVE EXAMPLE 12 | | TREND TO AGGLOMERATION |
| COMPARATIVE EXAMPLE 13 | | TREND TO AGGLOMERATION |

DECORATING POWDER COMPOSITION

TECHNICAL FIELD

The present invention relates to a decorating powder composition for decorating the surface of a solid cosmetic material such as eye shadow, foundation, and lipstick.

BACKGROUND ART

In solid cosmetic materials such as eye shadow, foundation, and lipstick, it is important to use a technique for decorating the surface of the cosmetic materials by means of, for example, patterns and letters using titanated mica (pearl agent) having gloss, or the like, in order to realize a beautiful appearance to attract consumer's attention.

As a technique for decorating the surface of a cosmetic material with a pattern or the like, an electrostatic screen printing method is known which a voltage is applied between a powder coating material on a screen and an object to be coated so as to charge the object and the powder, and an electrostatic force is used to adhere the powder coating material to the object to be coated. However, although the electrostatic screen printing method excels in terms of making it possible to perform printing without applying a pressure to the surface of the object to be coated, and also enabling printing on objects to be coated with rough surfaces, fine patterns and letters are likely to become unclear and this method cannot be used for decorating solid cosmetic materials.

Further, in the inkjet printing method in which the dispersion of a powder coating material is sprayed onto the object to be coated, when a powder coating material including titanated mica (pearl agent) having a large particle diameter is used, a nozzle for ejecting the dispersion is easily clogged by the powder, and such a method is not suitable for mass production as a printing method for decorating solid cosmetic materials.

Meanwhile, in a so-called letterpress printing method in which a powder coating material is adhered to a printing plate and the printing plate is pressed against the object to be coated to transfer the powder coating material to the surface of the object to be coated, a fine pattern can be represented, but since the amount of the powder coating material adhering to the printing plate is not uniform and the pattern is likely to become unclear, such a method cannot be said to be sufficient for decorating the surface of solid cosmetic materials.

Therefore, it is required to develop a decorating powder composition aimed at decoration of the surface of a solid cosmetic material, in particular, for obtaining a solid cosmetic material having a beautiful appearance which is surface-decorated with a glossy powder, and a decorating method using the decorating powder composition.

Citation List

Patent Literature

[PTL 1] Japanese Patent Application Publication No. 2000-317383

SUMMARY OF INVENTION

Technical Problem

It is an object of the present invention to provide a decorating powder composition for decorating the surface of a solid cosmetic material, in particular, for obtaining a solid cosmetic material having a beautiful appearance which is surface-decorated with a glossy powder, and a decorating method using the decorating powder composition.

Solution to Problem

The inventors of the present invention have conducted an investigation to attain the aforementioned object and have found that where a glossy powder which has been surface-treated with a silane compound or a silazane compound is transferred to the surface of a solid cosmetic material by using a printing plate, glossy patterns and letters can be finely and clearly printed. This finding led to the creation of the present invention.

That is, the present invention provides a decorating powder composition for decorating the surface of a solid cosmetic material, the decorating powder composition including a glossy powder which has been surface-treated with a silane compound or a silazane compound.

The present invention also provides a solid cosmetic material having a surface decorated with the above-mentioned decorating powder composition.

The present invention also relates to a method for decorating a solid cosmetic material, the method including: bringing a printing plate to which the above-mentioned decorating powder composition has been caused to adhere, into contact with the solid cosmetic material, and transferring the decorating powder composition to a surface of the solid cosmetic material for decoration.

Advantageous Effects of Invention

When the printing plate to which the decorating powder composition of the present invention has been caused to adhere is brought into contact with the surface of the solid cosmetic material and the decorating powder composition is transferred to the surface of the solid cosmetic material, it is possible to obtain the solid cosmetic material decorated with fine and clear patterns or letters.

BRIEF DESCRIPTION OF DRAWINGS

FIG. 4 shows the adhesion state of the powder to the printing plate (partially, photos in lieu of drawings).

DESCRIPTION OF EMBODIMENTS

Figure 1:
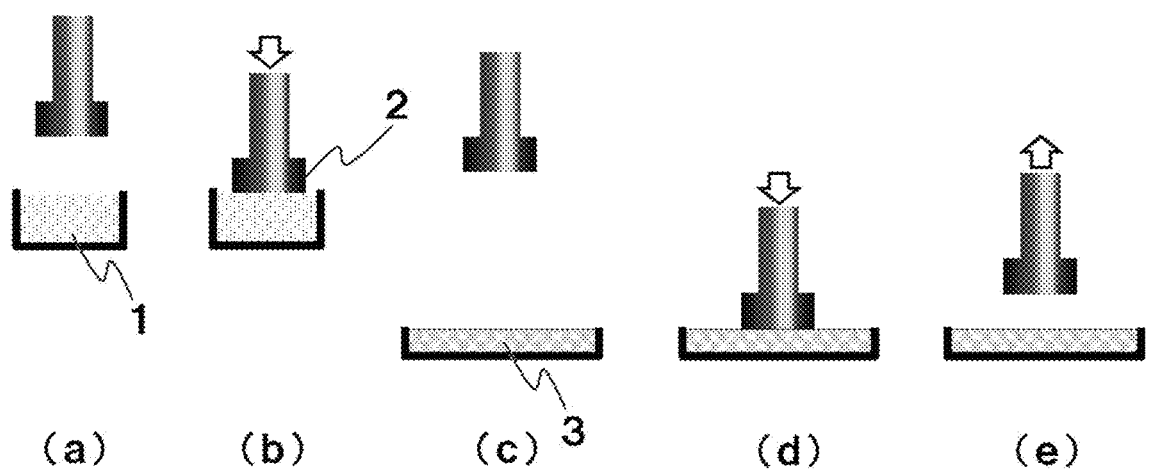
FIG. 1 is a schematic view illustrating a method for decorating a solid cosmetic material ((a) a stationary state; (b) a state in which a decorating powder composition is adhered to a printing plate; (c) a state in which a solid cosmetic product is arranged; (d) a state in which the decorating powder composition is printed on the surface of the solid cosmetic product; and (e) a state in which the decoration to the solid cosmetic product is completed).

The decorating powder composition of the present invention and the decorating method using the same will be described in detail hereinbelow.

The decorating powder composition includes a glossy powder which has been surface-treated with a silane compound or a silazane compound.

The glossy powder is a plate-like or spherical powder having an interference color, pearly luster, or metallic luster. Such powder is also generally called a pearl agent and is a general-purpose powder in the fields of paints and cosmetic materials. When the surface of a solid cosmetic material is decorated with the glossy powder, the pattern or letters obtained by decoration exhibits emphasized brightness and excellent aesthetic sensation can be given.

Examples of glossy plate-like powders include titanated mica, iron oxide-coated titanated mica, carmine-coated titanated mica, titanated mica coated with carmine and iron blue, titanated mica treated with iron oxide and carmine, titanated mica treated with iron blue, titanated mica treated with iron oxide and iron blue, titanated mica treated with chromium oxide, titanated mica treated with black titanium oxide, aluminum powder coated with acrylic resin, aluminum powder coated with silica, mica coated with titanium oxide, bismuth oxychloride coated with titanium oxide, talc coated with titanium oxide, mica coated with colored titanium oxide, synthetic mica coated with titanium oxide, silica coated with titanium oxide, alumina coated with titanium oxide, glass flakes coated with titanium oxide, polyethylene terephthalate-polymethyl methacfrylate laminated film powder, bismuth oxychloride, fish scale foil and the like.

Examples of the commercially available products include products manufactured by Merck KGaA, such as Timiron Splendid Gold™, Timiron Splendid Red™, Timiron Splendid Blue™, Timiron Splendid Green™, Timiron Super Red™, Timiron Super Blue™, Timiron Super Green™, Timiron Super Gold™, Colorona Sienna™, Colorona Passion Orange™, Colorona Carmin Red™, and Colorona Red Gold™; products manufactured by BASF SE such as Cloisonne Blue™, Cloisonne Green™, Cloisonne Gold™, Cloisonne Rouge Flambe™, Cloisonne Vivid Red™, Gemtone Tan Opal™, Gemtone Timica Brilliant Gold™, Timica Golden Bronze™, Timica Copper™, Duochrome RB™, Duochrome RY™, Duochrome YR™, Duochrome YB™, Duochrome BG™, Duochrome Duochrome BR™, Duochrome GY™, Flamenco Velvet™, Flamenco Satina™, Flamenco Red™, Flamenco Blue™, and Flamenco Gold™; products manufactured by Engelhard Corporation, such as Timica Brilliant Gold™, Timica Copper™, and Reflecks™ series; products manufactured by Topy Industries, Ltd., such as Helius R100S™ and Helios R100Y™; and products manufactured by Nippon Sheet Glass Co., Ltd., such as Metashine™ series and the like.

Examples of glossy spherical powders include composite powders obtained by coating the surface of spherical silicon dioxide, alumina, calcium carbonate, barium sulfate, Nylon, polyethylene, polystyrene, and poly(methyl methacrylate) with titanium dioxide, titanium oxide, zinc oxide, zirconium oxide, iron oxide, or the like. Such composite powders are disclosed in Japanese Patent Application Publication No. H11236315. The above lists are not limiting, and any spherical powder exhibiting gloss can be widely used as a component of the decorating powder composition.

The silane compound or silazane compound preferably has an alkyl group or a fluoroalkyl group having 1 to 20 carbon atoms and has reactivity with an inorganic oxide. Specific examples of the silane compound include hexyltrimethoxysilane, octyltrimethoxysilane, decyltrimethoxysilane, octadecyltrimethoxysilane, octyltriethoxysilane, trifluoropropyltrimethoxysilane, heptadecafluorodecyltrimethoxysilane, and the like. Of these, octyltriethoxysilane and octyltrimethoxysilane are particularly preferable. Specific examples of the silazane compound include hexamethyldisilazane, octyldisilazane, and the like among which octyldisilazane is particularly preferred.

A method for treating a glossy powder with a silane compound or a silazane compound is exemplified by a method involving mixing a silane compound or a silazane compound and a powder in an organic solvent such as n-hexane, cyclohexane, or a lower alcohol, optionally finely pulverizing, then removing the organic solvent by heating or decompression, and further heating at about 80° C. to 250° C. to chemically react the silane compound or the silazane compound on the surface of the powder, and a method involving mixing a silane compound or a silazane compound and a powder without a solvent, and heating at about 80° C. to 250° C. to chemically react the silane compound or the silazane compound on the surface of the powder. The surface-treated powders can be also used after optional crushing.

Powders surface-treated with a silane compound or a silazane compound are also commercially available. For example, an OTS-treated pigment, which is a product manufactured by Daito Kasei Kogyo Co., Ltd., can be also used as a powder surface-treated with n-octyltriethoxysilane.

The decorating powder composition used for decorating a solid cosmetic material can be constituted only by a glossy powder surface-treated with a silane compound or a silazane compound, or can be combined with another powder, pigment or the like. In this case, the amount of the surface-treated glossy powder to be blended in the decorating powder composition is not particularly limited, but in order to effectively exhibit the characteristics thereof, this amount is preferably in the range of 50% by weight to 100% by weight, and more preferably in the range of 80% by weight to 100% by weight.

The solid cosmetic material is not particularly limited as long as it is a cosmetic material in a solid form, such as make-up cosmetic materials such as foundation, eye shadow, lipstick and lip cream, and hair cosmetic materials such as hair stick. However, powder solid cosmetic materials such as foundation and eye shadow are particularly preferable as solid cosmetic materials for exhibiting a beautiful decorating effect with a glossy powder. Further, the solid cosmetic material is not limited by the molding method, and wet molded, dry molded, and oily molded products can be widely used.

As shown in FIG. 1, the method for decorating a solid cosmetic material involves lowering a printing plate (2) from a stationary state (state (a)), causing a decorating powder composition (1) to adhere to the printing plate surface (state (b)), bringing the printing plate into contact with the solid cosmetic material to transfer the decorating powder composition to the surface of the solid cosmetic material (states (c) and (d)), and completing the decoration of the solid cosmetic material (state (e)).

As a material of the printing plate, metals such as stainless steel and aluminum, and synthetic resins can be widely used. In addition, as long as the decorating powder composition can be caused to adhere to the printing plate and can thereafter be transferred to the solid cosmetic material surface, the printing plate is not limited to a specific printing method and a relief printing method, an offset printing method and the like can be widely used.

The decorating powder composition including a glossy powder which has been surface-treated with a silane compound or a silazane compound is smoothly transferred to the solid cosmetic while uniformly adhering to the printing plate, and demonstrates good adhesion to the surface of the solid cosmetic material. Therefore, it is possible to obtain an excellent decorating effect. Further, conventionally, it has been necessary to blend an oil component such as an ink material with a decorating pigment. However, by using the decorating powder composition, it is possible to perform excellent decoration with a glossy powder or with a mixed powder or a glossy powder and another powder, without blending an oily component.

EXAMPLES

The results of the confirmation tests of the effects obtained with the decorating powder composition of the present invention are described as examples.

An adhesion state of each decorating powder composition to a printing plate and a state after transferring the decorating powder composition from the printing plate to a solid cosmetic materials were observed with respect to the case in which a decorating powder composition including a pearl agent which has been surface-treated with octyltriethoxysilane was used (Example 1), the case in which a pearl agent which has been surface-treated with dimethicone was used (Comparative Example 1), and the case in which a pearl agent which has not been surface-treated was used (Comparative Example 2) (the formulation examples of the compositions are shown in Table 1).

The rouge of the formulation shown in Table 2 was used as the solid cosmetic material. The powdered components in the formulations 1 to 8 were mixed, the dissolved and mixed oily components 9 to 14 were mixed therewith, and ethanol was thereafter added to obtain slurry. The slurry was filled and molded in a middle dish, the surface was decorated with the pearl agent of Example 1 and Comparative Examples 1 and 2 and dried, and the rouge surface was observed to compare the states of the pearl agent transferred from the printing plate.

Figure 2:
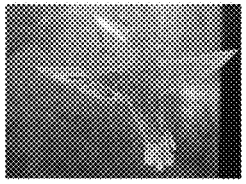
FIG. 2 shows the results of a comparative test of pearl agents with different surface treatment agents (photos in lieu of drawings).
Figure 3:
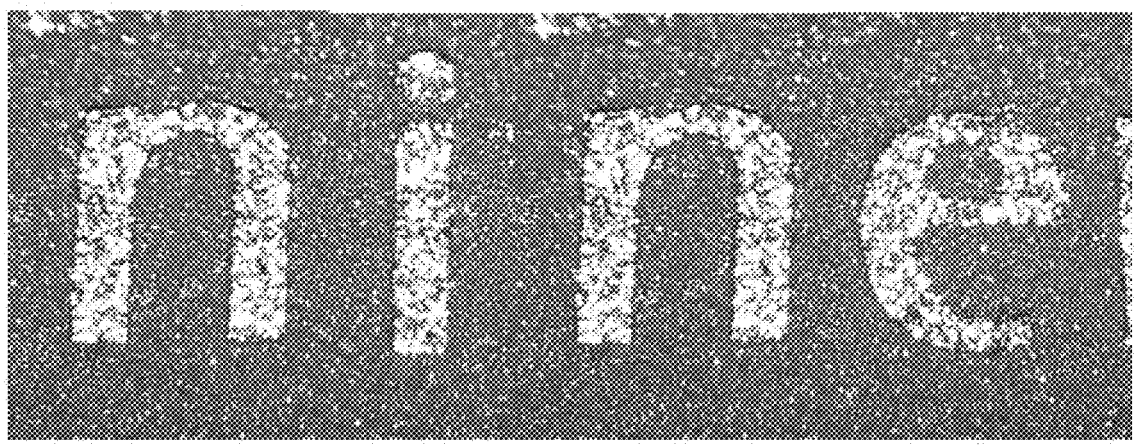
FIG. 3 shows the surface of the solid cosmetic material decorated with the decorating powder composition (photo in lieu of a drawing).

FIG. 2 shows the photograph of the surface of the printing plate before the adhesion of the pearl agent, the surface of the printing plate to which the respective pearl agent has adhered, and the surface of the decorated solid cosmetic material. It was confirmed that the pearl agent of Example 1 uniformly adhered to the printing plate, whereas the pearl agents of Comparative Example 1 and Comparative Example 2 did not adhere uniformly. Further, the pearl agent of Example 1 produced a fine and clear pattern on the surface of the rouge, whereas with the pearl agents of Comparative Examples 1 and 2, the amount of the pearl agent to be transferred was insufficient and a clear pattern could not be obtained. FIG. 3 shows another embodiment in which the surface of the rouge is decorated by drawing letters thereon by using the decorating powder composition of Example 1. In this case, a sufficient decorating effect could be confirmed.

TABLE 1

<Formulation: decorating powder composition (Example 1)>

| | Starting materials | Blended amount (% by mass) |
|---|---|---|
| 1 | Metashine MC1040RS (glass flakes coated with titanium oxide; manufactured by Nippon Sheet Glass Co., Ltd.) *1 | Appropriate amount |
| 2 | Cloisonne Sparkle Gold (mica coated with titanium oxide; manufactured by Engelhard Corporation) *1 | Appropriate amount |
| 3 | Cloisonne Vivid Red (titanated mica coated with iron oxide and iron blue; manufactured by BASF SE) *1 | Appropriate amount |
| | Total | 100 |

*1: surface treatment with octyltriethoxysilane

TABLE 2

<Formulation: Rouge>

| | Starting materials | Blended amount (% by mass) |
|---|---|---|
| 1 | Talc | Balance |
| 2 | Mica | 15 |
| 3 | Barium sulfate | 2 |
| 4 | Boron nitride | 5 |
| 5 | Spherical polyethylene powder | 2 |
| 6 | Methyl methacrylate cross-polymer powder | 3 |
| 7 | Colorant | Appropriate amount |
| 8 | Pearl agent | Appropriate amount |
| 9 | Vaseline | 5 |
| 10 | Tetra-2-ethylhexanoic acid pentaerythritol ester oil | 2 |
| 11 | Diisostearyl malate | 2 |
| 12 | Dimer-dilinoleic acid di(isostearyl-phytosteryl) | 2 |
| 13 | Methyl phenyl silicone | 2 |
| 14 | Sorbitan sesquiisostearate | 1 |
| | Total | 100 |

Further, for various kinds of pearl agents which were surface-treated with octyltriethoxysilane, the adhesiveness to the printing plate was evaluated. Where the adhesion of the powder to the printing plate is uneven, it is impossible to draw a pattern or letters on the surface of the solid cosmetic material, and the solid cosmetic material cannot be adequately decorated. In addition, where the powder aggregates and excessively adheres to the printing plate, when the printing plate is brought into contact with the solid cosmetic materials, the powder scatters and mass production becomes difficult.

TABLE 3

<Evaluation Criterion>

| | Surface treatment agent | Pearl agent | Adhesiveness to printing plate |
|---|---|---|---|
| Example 2 | Octyltriethoxysilane | Metashine MC1080RS *1 (glass flakes coated with titanium oxide) | ◯ |
| Example 3 | Octyltriethoxysilane | Metashine MC1080RY *1 (glass flakes coated with titanium oxide) | ◯ |
| Example 4 | Octyltriethoxysilane | Metashine MC1080RR *1 (glass flakes coated with titanium oxide) | ◯ |
| Example 5 | Octyltriethoxysilane | Metashine MC1080RB *1 (glass flakes coated with titanium oxide) | ◯ |
| Example 6 | Octyltriethoxysilane | Metashine MC1040RR *1 (glass flakes coated with titanium oxide) | ◯ |
| Example 7 | Octyltriethoxysilane | Metashine MC1040RY *1 (glass flakes coated with titanium oxide) | ◯ |
| Example 8 | Octyltriethoxysilane | Metashine MC1080RS *1 (glass flakes coated with titanium oxide) | ◯ |
| Example 9 | Octyltriethoxysilane | Metashine MC1040RS *1 (glass flakes coated with titanium oxide) | ◯ |
| Example 10 | Octyltriethoxysilane | Metashine MC1080RS *1 (glass flakes coated with titanium oxide) | ◯ |
| Example 11 | Octyltriethoxysilane | Duochrome GY *2 (mica coated with titanium oxide) | ◯ |
| Example 12 | Octyltriethoxysilane | Duochrome RY *2 (mica coated with titanium oxide) | ◯ |
| Example 13 | Octyltriethoxysilane | Colorona Passion Orange *3 (mica coated with titanium oxide) | ◯ |
| Example 14 | Octyltriethoxysilane | Colorona Sienna *3 (mica coated with titanium oxide) | ◯ |
| Example 15 | Octyltriethoxysilane | Helios R100S *4 (mica coated with titanium oxide) | ◯ |
| Example 16 | Octyltriethoxysilane | Helios R100Y *4 (mica coated with titanium oxide) | ◯ |
| Example 17 | Octyltriethoxysilane | Timica Brilliant Gold *2 (mica coated with titanium oxide) | ◯ |
| Example 18 | Octyltriethoxysilane | Timica Copper *2 (mica coated with titanium oxide) | ◯ |
| Example 19 | Octyltriethoxysilane | Timiron Super Gold *3 (mica coated with titanium oxide) | ◯ |
| Example 20 | Octyltriethoxysilane | Timiron Super Red *3 (mica coated with titanium oxide) | ◯ |
| Example 21 | Octyltriethoxysilane | Reflecks MD Changing Cherry *2 (glass flakes coated with titanium oxide) | ◯ |
| Example 22 | Octyltriethoxysilane | Cloisonne Vivid Red *5 (titanated mica coated with iron oxide and iron blue) | ◯ |

◯: Excellent (conforms)
*1 Product manufactured by Nippon Sheet Glass Co., Ltd.
*2 Product manufactured by Engelhard Corporation
*3 Product manufactured by Merck KGaA
*4 Product manufactured by Topy Industries, Ltd.
*5 Product manufactured by BASF SE As shown in Table 3, various pearl agents which surface-treated with octyltriethoxysilane exhibited excellent adhesiveness to the printing plate, and the appropriate amount of the pearl agent adhered to the printing plate was transferred to the surface of the solid cosmetic material. As a result, it was confirmed that glossy pattern or letters can be finely and clearly printed.

Further, Table 4 shows the results of evaluating the adhesiveness to the printing plate with respect to powders treated with various surface treatment agents.

TABLE 4

<Evaluation Criterion>

| | Surface treatment agent | Pearl agent | Adhesiveness to printing plate |
|---|---|---|---|
| Comparative Example 3 | Triethoxysilylethyl polydimethylsiloxyethyl hexyldimethicone | Talc | X |
| Comparative Example 4 | Magnesium stearate | Synthetic golden mica | X |
| Comparative Example 5 | Dextrin palmitate | Zinc oxide calcined at low temperature | X |
| Comparative Example 6 | Triethoxysilylethyl polydimethylsiloxyethyl dimethicone | Synthetic golden mica | X |
| Comparative Example 7 | Perfluorooctyl triethoxysilane - acrylic acid alkyl copolymer methyl polysiloxane ester and aluminum chloride | Talc | X |
| Comparative Example 8 | Nε-lauroyl-L-lycine | Synthetic golden mica | X |
| Comparative Example 9 | Distearyl dimethylammonium chloride | Synthetic golden mica | X |
| Comparative Example 10 | (No surface treatment) | Synthetic golden mica | X |
| Comparative Example 11 | n-Octyltriethoxysilane | Titanium oxide | X |
| Comparative Example 12 | Methicone | Titanium oxide | X |
| Comparative Example 13 | Dextrin palmitate | Zinc oxide calcined at low temperature | X |

X: Inferior (does not conform)

The powders of Comparative Examples 3 to 13 were all inferior in adhesiveness due to uneven adhesion to the printing plate and excessive adhesion to the printing plate caused by agglomeration of the powder. FIG. 4 shows a state in which the powders of Comparative Examples 3 to 13 were adhered to the printing plate.

REFERENCE SIGNS LIST

1 Decorating powder composition
2 Printing plate
3 Solid cosmetic material

The invention claimed is:

1. A method for decorating a solid cosmetic, the method comprising:
   bringing a lower surface of a printing plate into contact with a decorating powder composition and holding the solid cosmetic on the lower surface of the printing plate while the decorating powder composition remains in a powder state, the decorating powder composition comprising a glossy pearl agent which has been surface-treated with a silane compound or a silazane compound,
   bringing the lower surface of the printing plate into contact with the solid cosmetic, and
   transferring the decorating powder composition to a surface of the solid cosmetic for decoration.

2. The method for decorating a solid cosmetic according to claim 1,
   wherein the silane compound is selected from the group consisting of hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane, and
   the silazane compound is selected from the group consisting of hexamethyldisilazane and octyldisilazane.

3. A method for decorating a solid cosmetic, the method comprising:
   bringing a lower surface of a printing plate into contact with a decorating powder composition in a container, holding the solid cosmetic on the lower surface of the printing plate, and separating the lower surface of the printing plate from the container while the decorating powder composition remains in a powder state, the decorating powder composition comprising a glossy pearl agent which has been surface-treated with a silane compound or a silazane compound,
   bringing the lower surface of the printing plate into contact with the solid cosmetic, and
   transferring the decorating powder composition to a surface of the solid cosmetic for decoration.

4. The method for decorating a solid cosmetic according to claim 3,
   wherein the silane compound is selected from the group consisting of hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane, and
   the silazane compound is selected from the group consisting of hexamethyldisilazane and octyldisilazane.

* * * * *